US012575783B2

(12) United States Patent
Friedman et al.

(10) Patent No.: US 12,575,783 B2
(45) Date of Patent: Mar. 17, 2026

(54) SYSTEMS AND METHODS FOR SEIZURE DETECTION

(71) Applicant: Board of Regents, The University of Texas System, Austin, TX (US)

(72) Inventors: Joseph S. Friedman, Dallas, TX (US); Mehrdad Nourani, Richardson, TX (US); Hina Dave, Dallas, TX (US); Alexander J. Edwards, Melissa, TX (US); Xuan Hu, Plano, TX (US); Abbas A. Zaki, Plano, TX (US); Noah C. Parker, Denton, TX (US); Jay H. Harvey, Southlake, TX (US); Taeyoon Kim, Richardson, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 951 days.

(21) Appl. No.: 17/837,503

(22) Filed: Jun. 10, 2022

(65) Prior Publication Data

US 2022/0395217 A1      Dec. 15, 2022

Related U.S. Application Data

(60) Provisional application No. 63/209,837, filed on Jun. 11, 2021.

(51) Int. Cl.
*A61B 5/00*          (2006.01)
*A61N 1/36*          (2006.01)

(52) U.S. Cl.
CPC .......... *A61B 5/4094* (2013.01); *A61B 5/0006* (2013.01); *A61B 5/7225* (2013.01); *A61N 1/36064* (2013.01); *A61N 1/36139* (2013.01)

(58) Field of Classification Search
CPC . A61B 5/4094; A61B 5/0006; A61B 5/36064; A61N 1/36139
(Continued)

(56) References Cited

U.S. PATENT DOCUMENTS

| | | | |
|---|---|---|---|
| 8,641,646 B2 * | 2/2014 | Colborn | G16H 40/63 600/595 |
| 10,743,809 B1 * | 8/2020 | Kamousi | G06F 9/542 |

(Continued)

OTHER PUBLICATIONS

Zaki, AA, et al. "Analog Seizure Detection for Implanted Responsive Neurostimulation." arXiv preprint arXiv:2106.06590 (2021).
(Continued)

*Primary Examiner* — Suchin Parihar
(74) *Attorney, Agent, or Firm* — NORTON ROSE FULBRIGHT US LLP

(57)          ABSTRACT

Systems and methods to detect seizures using analog circuitry. One example method generally includes obtaining, at a seizure detection system, one or more electroencephalogram (EEG) signals, detecting a plurality of features associated with each of the one or more EEG signals, generating a bitstream indicating a seizure probability associated with each feature of the plurality of features to yield a plurality of bitstreams indicating a plurality of seizure probabilities, and generating a seizure detection output based on the plurality of bitstreams indicating the plurality of seizure probabilities of the plurality of features.

22 Claims, 13 Drawing Sheets

(58) Field of Classification Search

USPC .......................................................... 716/117

See application file for complete search history.

(56) References Cited

U.S. PATENT DOCUMENTS

| | | | | |
|---|---|---|---|---|
| 2006/0111644 | A1* | 5/2006 | Guttag | A61B 5/7267 |
| | | | | 600/544 |
| 2010/0121215 | A1* | 5/2010 | Giftakis | A61B 5/4094 |
| | | | | 600/595 |
| 2011/0054583 | A1* | 3/2011 | Litt | A61B 5/291 |
| | | | | 600/377 |
| 2011/0230730 | A1* | 9/2011 | Quigg | A61B 5/386 |
| | | | | 600/301 |
| 2014/0121554 | A1* | 5/2014 | Sarma | A61B 5/4094 |
| | | | | 600/544 |
| 2019/0059803 | A1* | 2/2019 | Myers | A61B 5/369 |
| 2019/0150774 | A1* | 5/2019 | Brinkmann | A61B 5/291 |
| 2019/0175028 | A1* | 6/2019 | Osorio | A61B 5/4836 |
| 2023/0270345 | A1* | 8/2023 | Osorio | A61B 5/0205 |
| | | | | 702/19 |

OTHER PUBLICATIONS

World Health Orginization. (Jun. 2019) Epilepsy. [Online]. Available: https://www.who.int/news-room/fact-sheets/detail/epilepsy.

Boon P, et al. "Neurostimulation for drug-resistant epilepsy: a systematic review of clinical evidence for efficacy, safety, contraindications and predictors for response." Current opinion in neurology 31.2 (2018): 198-210.

Assi EB, et al. "Towards accurate prediction of epileptic seizures: A review." Biomedical Signal Processing and Control 34 (2017): 144-157.

Davis P, et al. "Neuromodulation for the treatment of epilepsy: a review of current approaches and future directions." Clinical Therapeutics 42.7 (2020): 1140-1154.

Alomar SA, et al. "Different modalities of invasive neurostimulation for epilepsy." Neurological Sciences 41.12 (2020): 3527-3536.

Friedman JS, et al. "Bayesian inference with muller c-elements." IEEE Transactions on Circuits and Systems I: Regular Papers 63.6 (2016): 895-904.

NeuroPace. (Jun. 2020) RNS system physician manual. [Online]. Available: https://www.neuropace.com/wp-content/uploads/2021/02/neuropace-rns-system-manual-320.pdf.

Chen WM, et al. "A fully integrated 8-channel closed-loop neural-prosthetic CMOS SoC for real-time epileptic seizure control." IEEE journal of solid-state circuits 49.1 (2013): 232-247.

Pinto MF, et al. "A personalized and evolutionary algorithm for interpretable EEG epilepsy seizure prediction." Scientific reports 11.1 (2021): 3415.

Yoo J, et al. "An 8-channel scalable EEG acquisition SoC with patient-specific seizure classification and recording processor." IEEE journal of solid-state circuits 48.1 (2012): 214-228.

Altaf MA, et al. "A 16-channel patient-specific seizure onset and termination detection SoC with impedance-adaptive transcranial electrical stimulator." IEEE Journal of Solid-State Circuits 50.11 (2015): 2728-2740.

Gaines BR, Stochastic Computing Systems. Boston, MA: Springer US, 1969, pp. 37-172.

Hoe, DHK "Bayesian inference using stochastic logic: A study of buffering schemes for mitigating autocorrelation." International Journal of Approximate Reasoning 112 (2019): 4-21.

Zhou S, et al. "An ultra-low power CMOS random number generator." Solid-State Electronics 52.2 (2008): 233-238.

Yang K, et al. "A robust −40 to 120° C. all-digital true random number generator in 40nm CMOS." 2015 Symposium on VLSI Circuits (VLSI Circuits). IEEE, 2015.

Mathew SK, et al. "µ Rng: A 300-950 mV, 323 Gbps/W All-Digital Full-Entropy True Random Number Generator in 14 nm FinFET CMOS." IEEE Journal of Solid-State Circuits 51.7 (2016): 1695-1704.

Vodenicarevic D, et al. "Low-energy truly random number generation with superparamagnetic tunnel junctions for unconventional computing." Physical Review Applied 8.5 (2017): 054045.

Camsari KY, et al. "Stochastic p-bits for invertible logic." Physical Review X 7.3 (2017): 031014.

Camsari KY, et al. "Implementing p-bits with embedded MTJ." IEEE Electron Device Letters 38.12 (2017): 1767-1770.

Shah V, et al. "The temple university hospital seizure detection corpus." Frontiers in neuroinformatics 12 (2018): 83.

Shoaran M, et al. "Energy-efficient classification for resource-constrained biomedical applications." IEEE Journal on Emerging and Selected Topics in Circuits and Systems 8.4 (2018): 693-707.

Truong ND, et al. "Convolutional neural networks for seizure prediction using intracranial and scalp electroencephalogram." Neural Networks 105 (2018): 104-111.

Daoud H, et al. "Efficient epileptic seizure prediction based on deep learning." IEEE transactions on biomedical circuits and systems 13.5 (2019): 804-813.

Yang J, et al. "From seizure detection to smart and fully embedded seizure prediction engine: A review." IEEE Transactions on Biomedical Circuits and Systems 14.5 (2020): 1008-1023.

Muller R, et al. "A 0.013 mm2 , 5 µW , DC-Coupled Neural Signal Acquisition IC With 0.5 V Supply," in IEEE Journal of Solid-State Circuits, vol. 47, No. 1, pp. 232-243 (2012).

Xu X, et al. "A 1-V 450-nW fully integrated biomedical sensor interface system." 2008 IEEE Symposium on VLSI Circuits. IEEE, 2008.

Zou X, et al. "A 1V 22µW 32-channel implantable EEG recording IC." 2010 IEEE International Solid-State Circuits Conference—(ISSCC). IEEE, 2010.

Denison T, et al. "A 2.2/spl mu/W 94nV//spl radic/Hz, chopper-stabilized instrumentation amplifier for EEG detection in chronic implants." 2007 IEEE International Solid-State Circuits Conference. Digest of Technical Papers. IEEE, 2007.

Sun FT, et al. "The RNS System: responsive cortical stimulation for the treatment of refractory partial epilepsy." Expert review of medical devices 11.6 (2014): 563-572.

* cited by examiner

201

| $Q_N$ | $D_i$ | ⋮ | $D_3$ | $D_2$ | $D_1$ |
|---|---|---|---|---|---|
| 1 | 1 | ⋮ | 1 | 1 | 1 |
| 0 | 0 | ⋮ | 0 | 0 | 0 |
| $Q_{N-1}$ | ELSE | | | | |

*FIG. 2B*

| PATIENT | MEAN | MEAN(ABS) | RMS | HMOB | LINE LENGTH | ENERGY | INTEGRAL | VARIANCE |
|---|---|---|---|---|---|---|---|---|
| 2 | 1.0000 | 1.0000 | 1.0000 | 1.0000 | 1.0000 | 1.0000 | 1.0000 | 1.0000 |
| 258 | 0.9551 | 0.9648 | 0.9785 | 0.8867 | 0.9316 | 0.9180 | 0.9688 | 0.8789 |
| 302 | 0.9102 | 0.8945 | 0.8594 | 0.8750 | 0.8398 | 0.8789 | 0.8867 | 0.8945 |
| 1357 | 0.8878 | 0.8878 | 0.8827 | 0.8112 | 0.8724 | 0.8878 | 0.9082 | 0.8214 |
| 1543 | 0.8394 | 0.8686 | 0.7737 | 0.8467 | 0.7445 | 0.7153 | 0.8175 | 0.8248 |
| 1548 | 0.9356 | 0.9307 | 0.9703 | 0.8267 | 0.9356 | 0.9208 | 0.9406 | 0.9010 |
| 2297 | 0.8415 | 0.8470 | 0.8415 | 0.6776 | 0.9016 | 0.8087 | 0.8470 | 0.6503 |
| 3208 | 0.9533 | 0.7850 | 0.9720 | 0.9346 | 0.9439 | 0.7757 | 0.8972 | 0.8692 |
| 3401 | 0.9615 | 0.9231 | 0.9615 | 1.0000 | 1.0000 | 0.9231 | 0.9231 | 0.9231 |
| 3636 | 0.8788 | 0.8333 | 0.7424 | 0.7424 | 0.7424 | 0.8182 | 0.9091 | 0.6818 |
| 3977 | 0.8256 | 0.7674 | 0.7209 | 0.7267 | 0.8314 | 0.7733 | 0.8198 | 0.6512 |
| 4151 | 0.7805 | 0.7317 | 0.6890 | 0.7561 | 0.9085 | 0.8720 | 0.7805 | 0.6829 |
| 4892 | 0.9147 | 0.9479 | 0.9289 | 0.8009 | 0.8720 | 0.9384 | 0.8934 | 0.6019 |
| 5452 | 0.8918 | 0.8814 | 0.8969 | 0.8196 | 0.9175 | 0.8454 | 0.8989 | 0.9381 |
| 5625 | 0.8526 | 0.8526 | 0.8421 | 0.6526 | 0.8421 | 0.8632 | 0.7158 | 0.6421 |
| 5672 | 0.8654 | 0.8846 | 0.8846 | 0.8462 | 0.9327 | 0.7981 | 0.9038 | 0.7692 |
| 5804 | 0.7110 | 0.7414 | 0.6350 | 0.7034 | 0.7262 | 0.6730 | 0.7757 | 0.6654 |
| 5943 | 0.9654 | 0.9494 | 0.9570 | 0.7960 | 0.7892 | 0.9764 | 0.9511 | 0.8668 |
| 6351 | 0.6850 | 0.7874 | 0.8661 | 0.8740 | 0.8189 | 0.5906 | 0.7638 | 0.6535 |
| 6413 | 0.8196 | 0.9072 | 1.0000 | 0.7216 | 0.7577 | 0.8454 | 0.9433 | 0.8299 |
| 6507 | 0.8404 | 0.7394 | 0.8032 | 0.6755 | 0.7819 | 0.6436 | 0.7766 | 0.6596 |
| 6514 | 0.7622 | 0.6643 | 0.6783 | 0.5874 | 0.5804 | 0.6923 | 0.7343 | 0.5315 |
| 6904 | 0.8599 | 0.7626 | 0.6848 | 0.6809 | 0.8560 | 0.6926 | 0.8249 | 0.6654 |
| 7128 | 0.7965 | 0.7920 | 0.7920 | 0.6991 | 0.8407 | 0.9204 | 0.8451 | 0.7257 |
| 7234 | 0.7326 | 0.7442 | 0.8256 | 0.6163 | 0.6512 | 0.7907 | 0.7558 | 0.5465 |
| 7623 | 0.7364 | 0.8000 | 0.8273 | 0.9000 | 0.9636 | 0.8182 | 0.7364 | 0.8364 |

FEATURE

FIG. 6

| PATIENT | MEAN | ENERGY MEAN | MEAN ABSOLUTE | MEAN ENERGY |
|---|---|---|---|---|
| 2 | 0.544 | 0.5374 | 0.5495 | 0.5615 |
| 258 | 0.693 | 0.7194 | 0.6685 | 0.7226 |
| 302 | 0.3455 | 0.3169 | 0.339 | 0.3987 |
| 1357 | 0.7341 | 0.621 | 0.609 | 0.5925 |
| 1543 | 0.3583 | 0.3352 | 0.3316 | 0.3376 |
| 1548 | 0.9893 | 0.985 | 0.984 | 0.9842 |
| 2297 | 0.7042 | 0.6846 | 0.6822 | 0.6789 |
| 3208 | 0.331 | 0.3422 | 0.3662 | 0.4613 |
| 3401 | 0.6206 | 0.5111 | 0.7343 | 0.7495 |
| 3636 | 0.323 | 0.2956 | 0.3564 | 0.4205 |
| 3977 | 0.4478 | 0.4329 | 0.4527 | 0.4253 |
| 4151 | 0.622 | 0.3904 | 0.3966 | 0.3933 |
| 4456 | 0.916 | 0.9022 | 0.932 | 0.8958 |
| 4892 | 0.9217 | 0.7491 | 0.9478 | 0.7782 |
| 5452 | 0.3113 | 0.3303 | 0.2645 | 0.3156 |
| 5625 | 0.4746 | 0.4703 | 0.4735 | 0.4885 |
| 5672 | 0.8895 | 0.8873 | 0.8697 | 0.8851 |
| 5804 | 0.4642 | 0.4875 | 0.5022 | 0.5128 |
| 5943 | 0.755 | 0.4328 | 0.6465 | 0.5725 |
| 6351 | 0.3738 | 0.3711 | 0.3569 | 0.3668 |
| 6413 | 0.9792 | 0.9848 | 0.9733 | 0.986 |
| 6507 | 0.5812 | 0.5431 | 0.5425 | 0.5446 |
| 6514 | 0.3426 | 0.3021 | 0.3123 | 0.3186 |
| 6544 | 0.7845 | 0.7973 | 0.8159 | 0.7938 |
| 6904 | 0.4531 | 0.3978 | 0.4581 | 0.4791 |
| 7128 | 0.7663 | 0.6336 | 0.6506 | 0.6393 |
| 7234 | 0.4109 | 0.3878 | 0.4315 | 0.3875 |
| 7623 | 0.6724 | 0.6106 | 0.7304 | 0.7608 |

FEATURE

*FIG. 8*

| PATIENT | 1 | 2 | 3 | 4 |
|---|---|---|---|---|
| 2 | 0.5615 | 0.624 | 0.6317 | 0.6458 |
| 258 | 0.7226 | 0.7305 | 0.7391 | 0.7305 |
| 302 | 0.3987 | 0.4871 | 0.4871 | 0.5233 |
| 1357 | 0.7341 | 0.7833 | 0.7824 | 0.7833 |
| 1543 | 0.3583 | 0.494 | 0.5809 | 0.6242 |
| 1548 | 0.9893 | 0.9905 | 0.9918 | 0.9905 |
| 2297 | 0.7042 | 0.7809 | 0.8084 | 0.8273 |
| 3208 | 0.4613 | 0.5541 | 0.5896 | 0.6273 |
| 3401 | 0.7495 | 0.8521 | 0.8669 | 0.8744 |
| 3636 | 0.4205 | 0.4691 | 0.4691 | 0.4691 |
| 3977 | 0.4527 | 0.5053 | 0.5396 | 0.5092 |
| 4151 | 0.622 | 0.6832 | 0.7041 | 0.6908 |
| 4456 | 0.932 | 0.7881 | 0.8458 | 0.7877 |
| 4892 | 0.9478 | 0.9594 | 0.9588 | 0.9657 |
| 5452 | 0.3303 | 0.4065 | 0.4267 | 0.4804 |
| 5625 | 0.4885 | 0.6272 | 0.7183 | 0.7387 |
| 5672 | 0.8895 | 0.9423 | 0.9569 | 0.9759 |
| 5804 | 0.5128 | 0.5189 | 0.5361 | 0.555 |
| 5943 | 0.755 | 0.7932 | 0.8028 | 0.821 |
| 6351 | 0.3738 | 0.503 | 0.5633 | 0.5599 |
| 6413 | 0.986 | 0.9894 | 0.9906 | 0.9895 |
| 6507 | 0.5812 | 0.6849 | 0.7244 | 0.7722 |
| 6514 | 0.3426 | 0.4576 | 0.4677 | 0.4915 |
| 6544 | 0.8159 | 0.7646 | 0.7692 | 0.7813 |
| 6904 | 0.4791 | 0.5319 | 0.5571 | 0.5612 |
| 7128 | 0.7663 | 0.8318 | 0.8318 | 0.8602 |
| 7234 | 0.4315 | 0.4765 | 0.5189 | 0.4765 |
| 7623 | 0.7608 | 0.8677 | 0.8861 | 0.8998 |

NUMBER OF FEATURES/CHANNELS USED FOR INFERNCE

*FIG. 9*

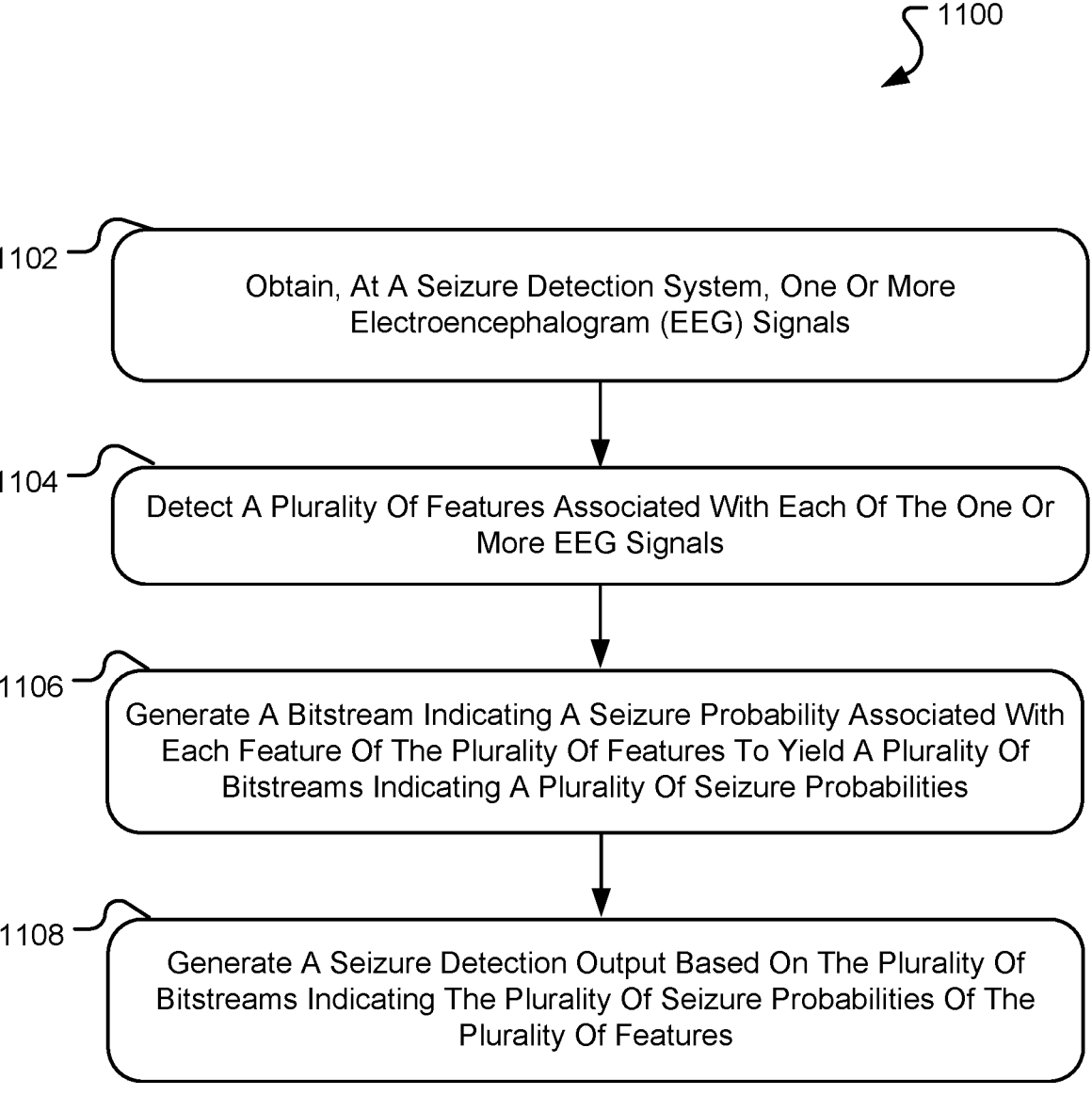

1100

1102 — Obtain, At A Seizure Detection System, One Or More Electroencephalogram (EEG) Signals 1104 — Detect A Plurality Of Features Associated With Each Of The One Or More EEG Signals 1106 — Generate A Bitstream Indicating A Seizure Probability Associated With Each Feature Of The Plurality Of Features To Yield A Plurality Of Bitstreams Indicating A Plurality Of Seizure Probabilities 1108 — Generate A Seizure Detection Output Based On The Plurality Of Bitstreams Indicating The Plurality Of Seizure Probabilities Of The Plurality Of Features

FIG. 11

SYSTEMS AND METHODS FOR SEIZURE DETECTION

CROSS-REFERENCE TO RELATED APPLICATION

This application claims the benefit of U.S. Provisional Patent Application No. 63/209,837 filed Jun. 11, 2021, which is incorporated by reference herein in its entirety.

BACKGROUND

1. Field

Aspects of the present inventive concept relate to systems and methods for seizure detection, and more particularly, to systems and techniques for seizure detection using analog circuitry.

2. Discussion of Related Art

As one of the most common neurological conditions, epilepsy affects 50 million people worldwide. Epilepsy is characterized by recurrent seizures resulting from excessive electrical discharges in either focal or generalized regions of the brain. Seizure types can vary from brief lapses of attention to muscle jerks and debilitating convulsions. Approximately 30% of epileptic patients suffer from refractory or drug-resistant epilepsy. Surgical resection is the conventional approach to treating drug-resistant focal epilepsy. If surgical resection is not possible, a neuromodulatory device can be offered to the patient.

SUMMARY

Certain aspects of the present inventive concept are directed to a method to detect seizures. The method generally includes obtaining, at a seizure detection system, one or more electroencephalogram (EEG) signals, detecting a plurality of features associated with each of the one or more EEG signals, generating a bitstream indicating a seizure probability associated with each feature of the plurality of features to yield a plurality of bitstreams indicating a plurality of seizure probabilities, and generating a seizure detection output based on the plurality of bitstreams indicating the plurality of seizure probabilities of the plurality of features.

Certain aspects of the present inventive concept are directed to an apparatus to detect seizures. The apparatus generally includes a feature detection circuit configured to detect a plurality of features associated with one or more EEG signals; a bitstream generator configured to generate a bitstream indicating a seizure probability associated with each feature of the plurality of features to yield a plurality of bitstreams indicating a plurality of seizure probabilities; and feature evaluation circuitry configured to generate a seizure detection output based on the plurality of bitstreams indicating the plurality of seizure probabilities of the plurality of features.

Certain aspects of the present inventive concept are directed to a seizure detection system. The seizure detection system generally includes one or more electrodes configured to generate one or more EEG signals; an amplification circuit configured to amplify the one or more EEG signals to yield one or more amplified EEG signals; a feature detection circuit configured to detect a plurality of features associated with each of the one or more amplified EEG signals; a bitstream generator configured to generate a bitstream indicating a seizure probability associated with each feature of the plurality of features to yield a plurality of bitstreams indicating a plurality of seizure probabilities; and feature evaluation circuitry configured to generate a seizure detection output based on the plurality of bitstreams indicating the plurality of seizure probabilities of the plurality of features.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 2B illustrates a truth table associated with a C-element circuit, in accordance with certain aspects of the present inventive concept.

FIG. 6 illustrates a windowed single feature performance of the seizure detection system, in accordance with certain aspects of the present inventive concept.

FIG. 8 illustrates an analog single feature performance of the seizure detection system, in accordance with certain aspects of the present inventive concept.

FIG. 9 illustrates an analog multi feature performance of the seizure detection system, in accordance with certain aspects of the present inventive concept.

FIG. 11 is a flow diagram illustrating example operations to detect seizures, in accordance with certain aspects of the present inventive concept.

Figure 1:
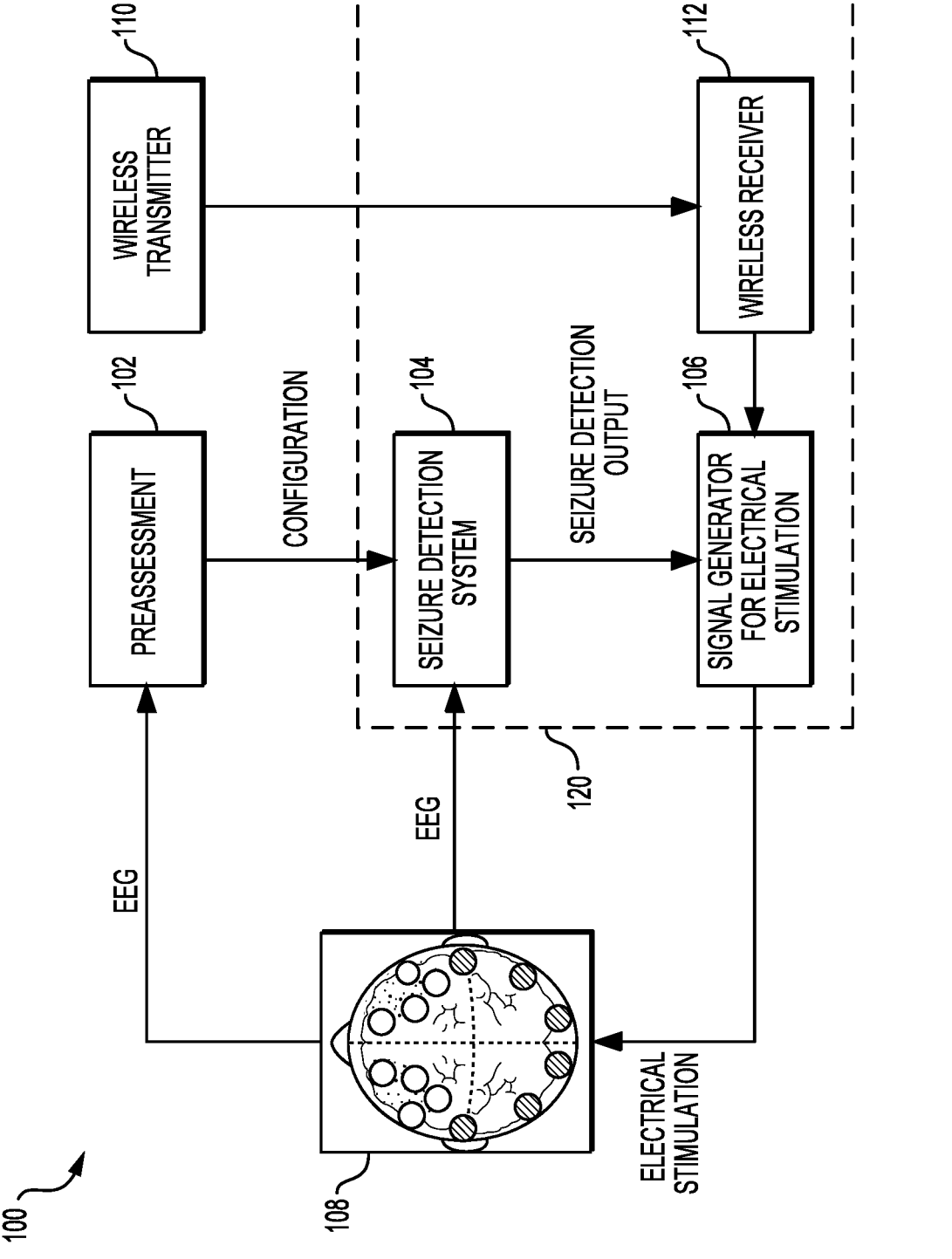
FIG. 1 is a block diagram illustrating example operations for seizure detection and mitigation, in accordance with certain aspects of the present inventive concept.

It will be apparent to one skilled in the art after review of the entirety disclosed that the steps illustrated in the figures listed above may be performed in other than the recited order, and that one or more steps illustrated in these figures may be optional.

DETAILED DESCRIPTION

Certain aspects of the present inventive concept provide apparatus and techniques for seizure detection and mitigation for epilepsy patient. Epilepsy may be treated with medication. However, many (e.g., 30%) of epileptic patients may be drug resistive. Resective surgery is not an option for all patients suffering from drug-resistant epilepsy especially if the seizures lack a well-defined epileptogenic region or if the region is in the eloquent cortex/deep brain structures. Furthermore, some patients continue to have seizures even after surgical resection. Devices like responsive neurostimulation systems may be implanted in select patients who may not be amenable to surgical resection. However, state-of-the-art devices suffer from low accuracy, limited contact points for treatment, algorithm development over a period of years to months dependent on user and patient, and high sensitivity. As surgical resection is not always possible or helpful, implantable neuromodulatory devices may be used to deliver electrical stimulations to targeted regions of the brain to reduce or mitigate seizures. Two intracranial options include deep brain stimulation (DBS) and responsive neurostimulation. The DBS device may be an open-loop system acting similar to a pacemaker offering regular pulses with no feedback from sensors in the brain. In contrast, responsive neurostimulation devices measure neural activity and offer stimulation when seizure activity is detected. Historically there has been a two-fold trade-off between detecting as many seizures as possible and not overstimulating the patient without compromising battery life. In extreme cases, embedded deep learning models for seizure detection may be used, which may have high power consumption. On the other extreme, some systems have limited to no seizure detection relying on over-stimulation to catch more seizure activity.

Certain aspects of the present inventive concept provide a seizure detection system with improved accuracy and reduced power consumption. The seizure detection system may be based on naïve Bayesian inference using Muller C-elements (C-Es). The seizure detection system may be patient specific. For instance, features and thresholds used for seizure detection may be tailored to a specific patient. The seizure detection system improves conventional neurostimulation devices by implementing analog signal processing for feature extraction, reducing power consumption as compared to conventional implementations using digital processing techniques.

The seizure detection system described herein takes advantage of seizure activity often being distributed in various networks throughout the brain. The seizure detection system provides multiple low-power inferences from several EEG channels, combining potentially disagreeing evidence with a low-power Bayesian inference engine comprising C-elements and stochastic bitstreams. The seizure detection system provides high detection accuracy at low power consumption resulting in increased battery life. The seizure detection system provides accurate (e.g., 98%) seizure detection by integrating multiple channels and features. The seizure detection system may have a power consumption of as little as 6.5 µW per channel, which as compared to conventional implementations, that would increase the battery life of an implantable device, including the seizure detection system, by up to 50%.

FIG. 1 is a block diagram illustrating example operations 100 for seizure detection and mitigation, in accordance with certain aspects of the present inventive concept. In some aspects of the present inventive concept, prior to implanting a seizure detection system for a patient, at block 102, a preassessment of the patient may be performed to personalize the configuration of the seizure detection system for the patient. For instance, based on EEG signals collected using electrodes on patient 108, a subset of candidate features may be selected that are determined to provide relatively more reliable seizure detection for the patient. As one example, a subset of relevant discriminatory signals (e.g., signals from epileptogenic zones) may be selected. Based on the selected signals, the subset of features may be selected to be used for personalized feature detection for the patient. In some cases, various thresholds or ranges for feature detection may also be selected for the patient, as described in more detail herein. For example, a particular measurement may be compared to the threshold (or determined to be within the range) to detect a particular feature associated with the EEG signal.

Once the personalized features, thresholds, or ranges have been selected during preassessment, a seizure detection system 104 may be configured to use the selected features, thresholds, or ranges. Once configured, the seizure detection system 104 may be implanted for the patient 108 with electrodes facilitating the collection of EEG signals. Based on the EEG signals, the seizure detection system 104 detects the occurrence of a seizure for the patient 108 and provides a seizure detection output to a signal generator 106 for electrical stimulation. The signal generator 106 generates electrical stimulation signals that may be applied to the brain of the patient using electrodes to mitigate (or at least reduce) seizure activity. In some aspects, the seizure detection system 104 and signal generator 106 may be part of a processing device 120 (e.g., implantable device) which may be implanted for the patient.

In some aspects, the processing device 120 may be implanted and include a wireless receiver 112, allowing the processing device 120 to receive wireless signals from external devices. For example, a wireless transmitter 110 may transmit a signal to the wireless receiver 112. The signal transmitted to the wireless receiver 112 may include a tuning signal which may be provided to the signal generator 106 and used to tune the electrical stimulation signal provided to the patient for seizure mitigation. In some aspects of the present inventive concept, the seizure detection system 104 may be implemented using a C-E circuit for Bayesian inference, as described in more detail with respect to FIGS. 2A, 2B, and 2C.

Figure 2A:
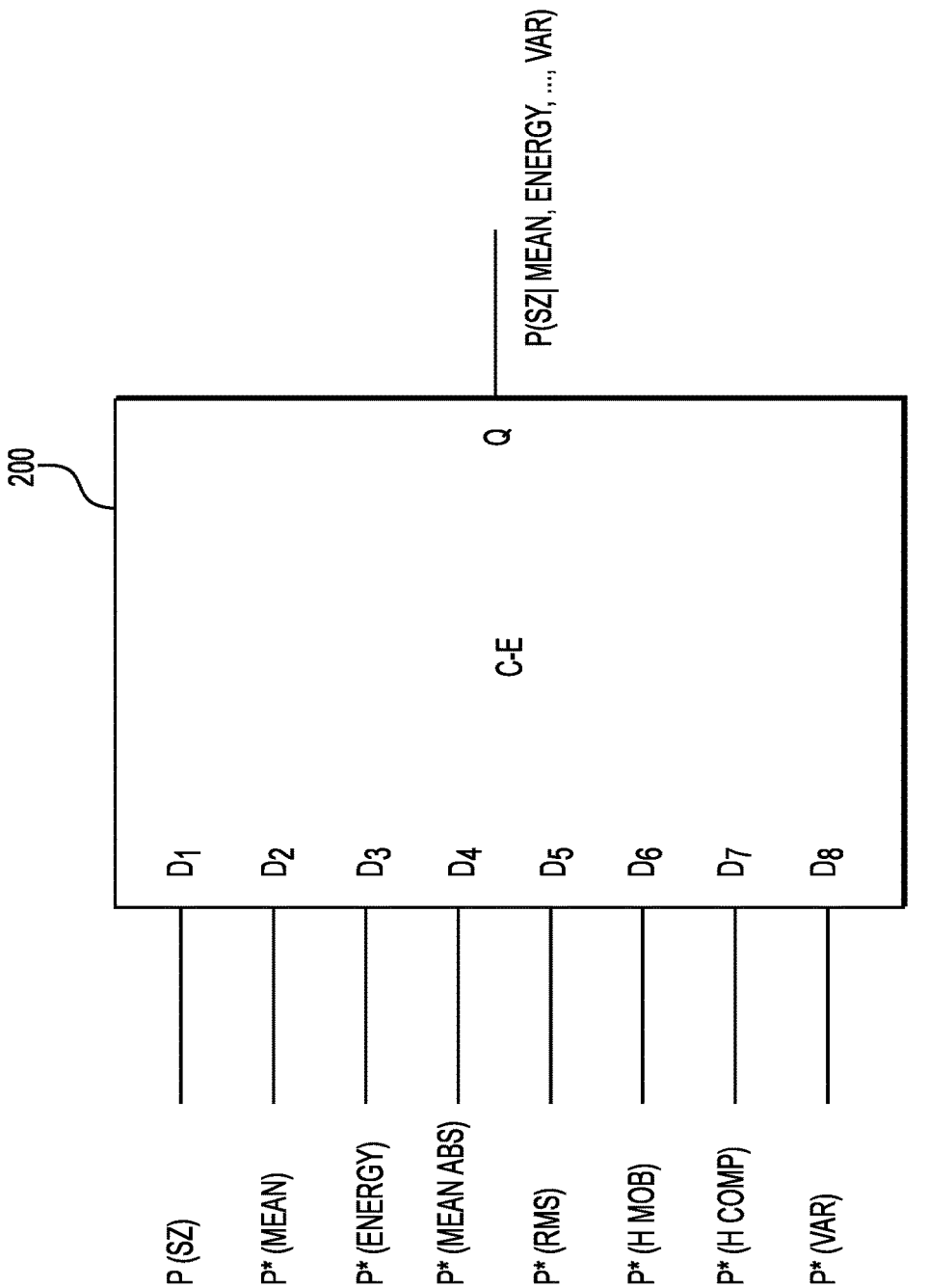
FIG. 2A illustrates a multi-input C-element for Bayesian inference, in accordance with certain aspects of the present inventive concept.

FIG. 2A illustrates a multi-input C-E circuit 200 for Bayesian inference, in accordance with certain aspects of the present inventive concept. As shown, the C-E circuit 200 receives digital inputs (labeled D1 to D8), each of the digital inputs being associated with a feature identified based on EEG signals indicating brain activity. While eight digital inputs are shown in FIG. 2A to facilitate understanding, any number of digital inputs may be used (e.g., D1 to Di, i being any integer greater than 1). As used herein, EEG signals generally refer to any signaling indicating brain activity which may be collected using surface (e.g., scalp-mounted) electrodes or implanted electrodes. For example, EEG signals may include intracranial EEG (iEEG) signals collected from surgically implanted electrodes or stereo EEG signals collected from electrodes implanted using a minimally invasive procedure.

As shown, the digital inputs may include bitstreams, each indicating a probability. The probabilities indicated by the bitstreams may include a seizure probability associated with each of various features including mean, energy mean, mean absolute, root mean square (RMS), Hjorth mobility, Hjorth complexity, or variance derived from EEG signals. One of the bitstreams may also provide a general seizure probability P(SZ). The C-E circuit 200 generates an output that indicates a probability of seizure given the detected input features (e.g., P(SZ|features)).

FIG. 2B illustrates a truth table 201 associated with the C-E circuit 200, in accordance with certain aspects of the present inventive concept. As shown, at each particular point in time, the C-E circuit 200 compares the logic state of the digital inputs, and if all the digital inputs are logic high, provides an output that is logic high. If all the digital inputs are logic low, the C-E circuit 200 provides an output that is logic low. Otherwise, if the digital inputs have different logic states (e.g., if any digital input has a logic state that is different than any other digital input), the C-E circuit 200 maintains the previous state (e.g., the output of the C-E circuit 200 remains unchanged).

Figure 2C:
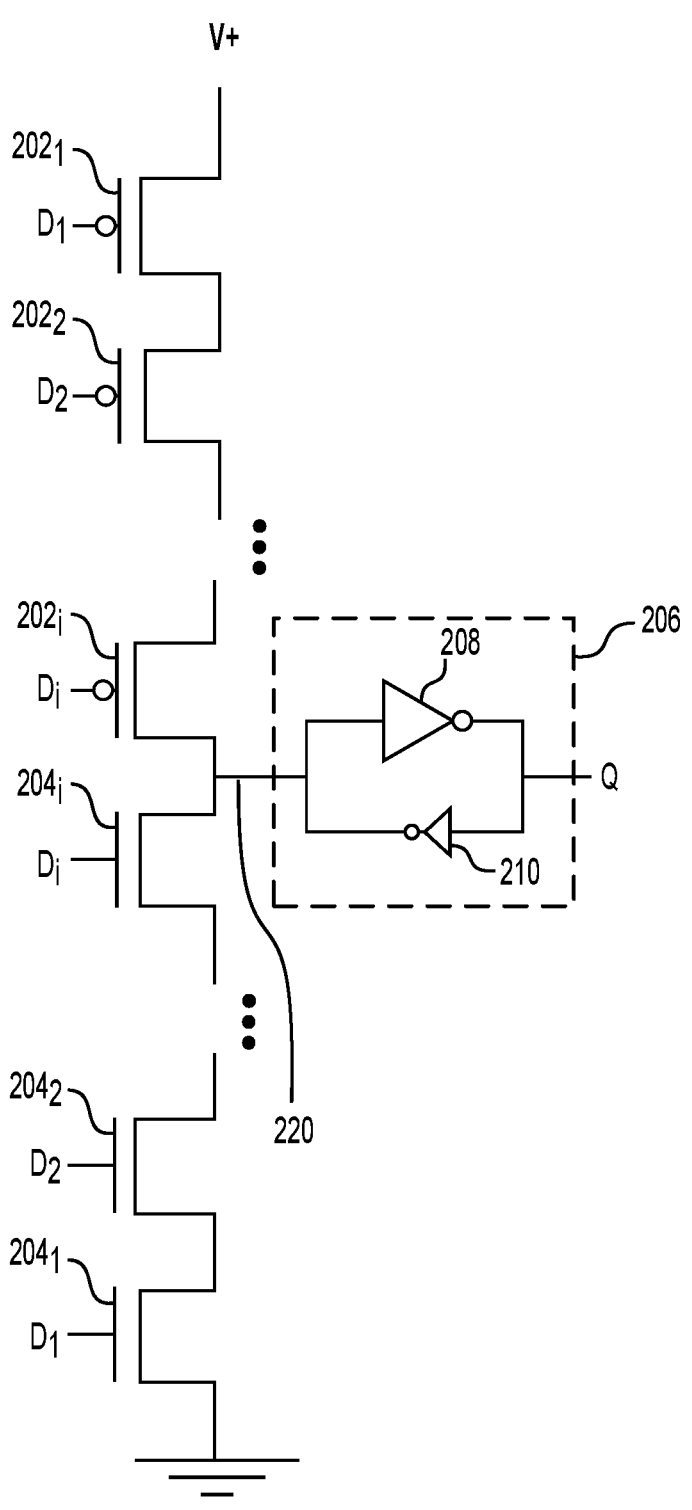
FIG. 2C illustrates an example implementation of a C-element circuit, in accordance with certain aspects of the present inventive concept.

FIG. 2C illustrates an example implementation of the C-E circuit 200, in accordance with certain aspects of the present inventive concept. As shown, the C-E circuit 200 includes p-channel metal-oxide-semiconductor (PMOS) transistors 202₁, 202₂, to 202ᵢ (collectively referred to as PMOS transistors 202) and n-channel metal-oxide-semiconductor (NMOS) transistors 204₁, 204₂, to 204ᵢ (collectively referred to as NMOS transistors 204). While the example C-E circuit 200 shown in FIG. 2C is implemented using NMOS and PMOS transistors, any suitable switch or transistor type may be used. As shown, a latch 206 is coupled between a common node 220 and the output (e.g., at output labeled "Q") of the C-E circuit 200. The latch 206 includes cross-coupled inverters 208, 210, as shown.

The gates of the PMOS transistors 202 receive the digital inputs D1 to Di, respectively, and the gates of the NMOS transistor 204 receive the digital inputs D1 to Di. Thus, if all the digital inputs D1 to Di are logic low, the PMOS transistors 202 are turned on, coupling a common node 220 to a voltage rail (V+). The logic state at the common node 220 is inverted via the latch 206, providing a logic low output. If all the digital inputs D1 to Di are logic high, the NMOS transistors 204 are turned on, coupling the common node 220 to a reference potential node (e.g., electrical ground) and providing a logic high output. If only some of the digital inputs D1 to Di are logic high or logic low, then the current state at the output of the C-E circuit 200 is maintained via the latch 206.

The C-E circuit 200 effectively implements a Bayesian inference. Bayesian inference computes the probability of an event V (e.g., a seizure) given the n observed evidences $E_1^m$, $E_2^m$, . . . $E_n^m$ (e.g., detected features) where m is the observed value of the corresponding evidence. For example, $P(E_3^{0.5})$ corresponds to the probability that evidence 3 has the value of 0.5. With this notation, naïve Bayesian inference is formulated as:

$$P(V \mid E_1^m, \dots , E_i^m) = \frac{P(V)\prod_{x=1}^{i} P^*(E_x^m)}{P(V)\prod_{x=1}^{i} P^*(E_x^m) + P(\overline{V})\prod_{x=1}^{i} (1 - P^*(E_x^m))}, \quad (1)$$

where $P^*(E_x^m)$ is defined as $$P^*(E_x^m) = \frac{P(E_x^m \mid V)}{P(E_x^m \mid V) + P(E_x^m \mid \overline{V})}. \quad (2)$$

The C-E circuit 200 implements a stochastic computation. Real numbers in [0, 1] are encoded as the probability that at any given time the state of a stochastic bitstream will be 1. Stochastic computing offers a way of computing mathematical operations. For instance, an AND gate can perform multiplication and a multiplexer (MUX) can be used for weighted addition. A multi-input Willer C-E block in the stochastic regime can compute the function:

$$Q = \frac{\prod_{x=1}^{i} D_x}{\prod_{x=1}^{i} D_x + \prod_{x=1}^{i} (1 - D_x)}$$

Which when the $D_x$ values are interpreted as P(V) and $P^*(E_x^m)$, directly implements equation (1). Thus, a single multi-input C-E circuit may implement a Bayesian inference in the stochastic regime. Using the C-E circuit may result in a reduction of energy usage to the order of nJ per-inference.

For high-accuracy and low-power seizure detection, multiple low-power features across different channels may be analyzed and integrated using a low-power inference. Thus, some aspects of the present inventive concept implement seizure detection without usage of high-power analog-to-digital conversion (ADC) and digital signal processing (DSP) blocks. Instead, seizure detection is implemented by making use of analog and stochastic blocks for energy-efficient, high-accuracy seizure detection. To enable low-power seizure detection avoiding DSP computations and ADCs, analog processing blocks are used, as described in more detail with respect to FIG. 3.

Figure 3:
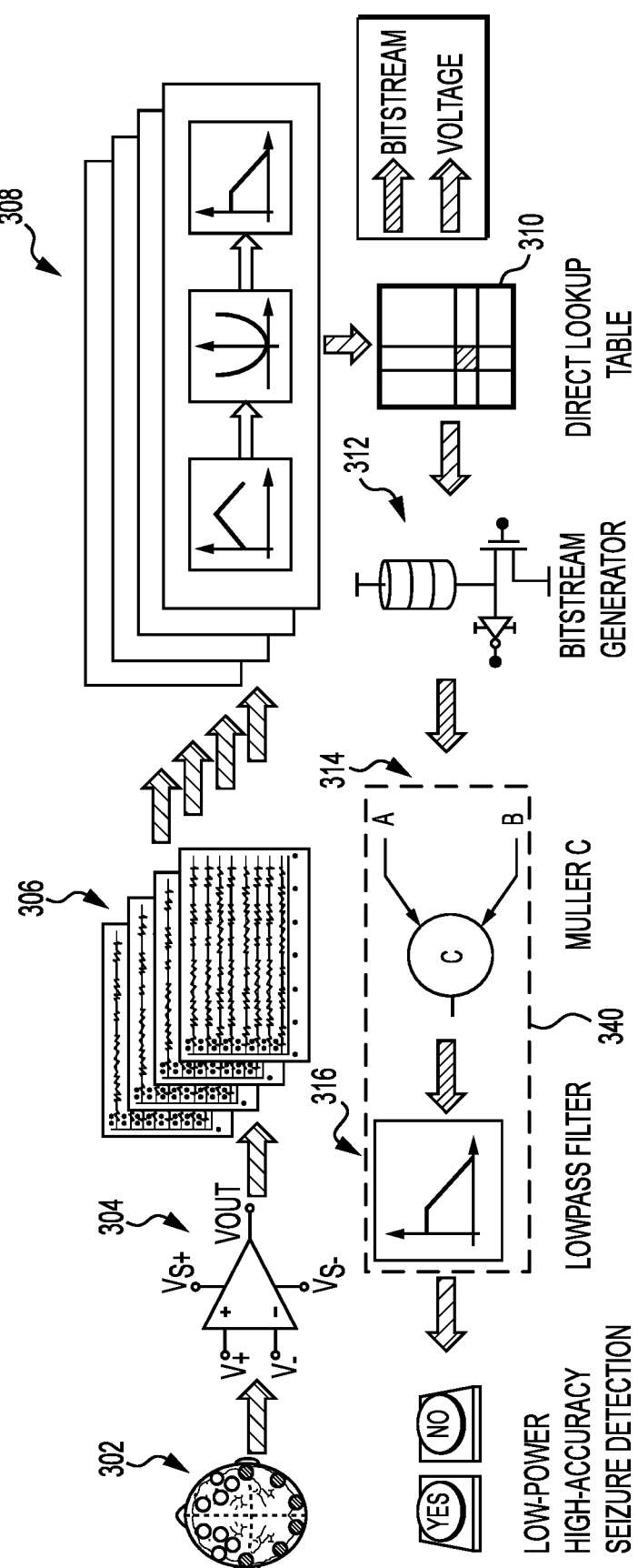
FIG. 3 depicts an example implementation of the seizure detection system, in accordance with certain aspects of the present inventive concept.

FIG. 3 depicts an example implementation of the seizure detection system, in accordance with certain aspects of the present inventive concept. A data path from EEG signal extraction to seizure identification is shown in FIG. 3. As shown, electrodes 302 may be used to collect EEG signals, which may be provided to an amplification system 304 to generate amplified EEG signals 306. As shown, EEG signals from multiple channels (e.g., multiple electrodes or multiple sense elements of an electrode) may be gathered.

The amplified EEG signals may be provided to a feature detection circuit 308. The feature detection circuit 308 may include circuitry that measures various features, such as mean or variance, and compares the measured feature to a threshold. For example, the mean of each of the EEG signals 306 may be measured and compared to a mean threshold. If the measured mean of the EEG signal meets the threshold, the feature detection circuit 308 outputs an indication of the detected feature to an analog voltage generation circuit 310.

The analog voltage generation circuit 310 may be implemented as a direct look up table outputting an analog voltage corresponding to a seizure probability associated with each detected feature. For example, suppose a detected mean feature is detected and the detected mean feature is associated with a 50% seizure probability. In that case, the analog voltage generation circuit 310 generates a 0.5 volt signal assuming a 1 volt rail to rail voltage.

The analog voltages indicating probabilities of each of the detected features are then provided to a bitstream generator 312. The bitstream generator 312 generates bitstreams indicating the seizure probabilities of the detected features. The bitstream generator 312 may generate a bitstream wherein a quantity of bits, in a particular time period, that have a specific logic state (e.g., logic high) indicate the seizure probability. For example, for the detected mean feature having a 50% seizure probability, the bitstream generator 312 may generate a bitstream where half the bits of the bitstream are logic high and half the bits of the bitstream are logic low. In some aspects, the bitstream generator 312 may be implemented as a voltage-controlled tunable random number generator (RNG) that produces stochastic bitstreams with a time-varying probability equal to the seizure probability of the associated feature. That is, the probability that each bit at the output of the bitstream generator is logic high may be equal to the seizure probability of the associated feature.

The generated bitstreams are then provided to feature evaluation circuitry 340, which may include a C-E circuit 314 and filter 316, in some aspects. The generated bitstreams may be provided as respective inputs of the C-E circuit 314 (e.g., corresponding to C-E circuit 200 as described with respect to FIGS. 2A, 2B, and 2C).

Figure 4:
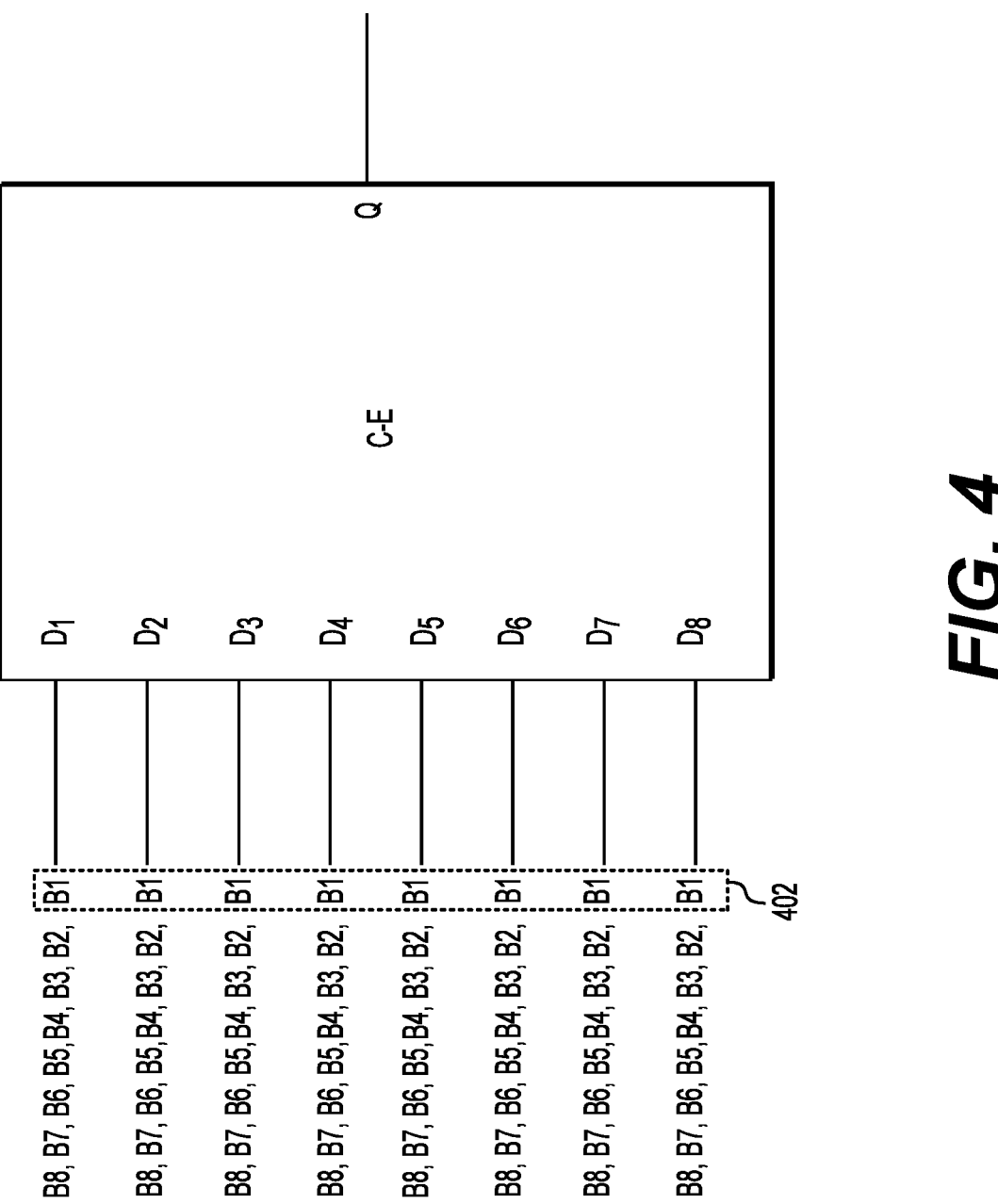
FIG. 4 illustrates bitstreams provided as digital inputs to a C-element circuit, in accordance with certain aspects of the present inventive concept.

FIG. 4 illustrates bitstreams provided as digital inputs to the C-E circuit 200, in accordance with certain aspects of the present inventive concept. As shown, the C-E circuit 200 compares corresponding bits (e.g., first bits 402, shown as "b1") of the digital inputs D1 to Dn. As described with respect to FIG. 2B, if all the bits 402 are logic high, then the output of the C-E circuit will be set to logic high, and if all the bits 402 are logic low, then the output of the C-E circuit will be set to logic low. Otherwise, the current logic state at the output of the C-E circuit is maintained. This process is performed for each of the corresponding bits of the bitstreams (e.g., second bits labeled "b2", then third bits labeled "b3", and so on).

Referring back to FIG. 3, the output of the C-E circuit 314 is provided to a filter (e.g., a low-pass filter), which generates a filtered analog voltage based on the digital output of the C-E circuit 314, as shown. The filtered analog voltage may be compared to a threshold. If the filtered analog voltage meets the threshold, the seizure detection system may output a seizure detection output (e.g., logic high) indicating a detected seizure. As described with respect to FIG. 1, the seizure detection output may be provided to signal generator 106 to initiate electrical stimulation of the brain of the patient to mitigate the detected seizure.

As described, the seizure detection system provides techniques for detecting a seizure with reduced power consumption as compared to conventional implementations. To reduce power usage, the system will not store or transmit EEG data. Rather, an implantable device includes the seizure detection system, facilitating seizure detection without transmission of EEG data to an external processor. Thus, before surgery, copious information about the patient's seizure networks may be gathered, and proper EEG channels, associated features, and thresholds may be identified and tuned before implantation surgery, as described herein. In some implementations, the number of (feature, channel) pairs that may be extracted for high-accuracy detection may vary from one to four depending on the patient. This pre-surgery study of the patient may also govern the placement of probes in the brain. EEG voltage signals range from hundreds of micro-volts to tens of milli-volts and information may be encoded in frequency bands of tens of hertz to hundreds of hertz. These low-frequency and low-voltage signals can be amplified by a low-noise differential amplifier (e.g., amplification system 304) to produce an analyzable rail-to-rail signal. In some aspects, one amplifier may be used per channel analyzed.

As described herein, once the EEG signals are obtained, the EEG signals are fed into one feature detection circuit 308 for detection of several types of features including mean, energy, mean of absolute value, line length, or Hjorth mobility. The detection of each feature via the feature detection circuit 308 may be via a low-power approximate analog implementation to avoid the high power cost of using a DSP. Detection of many features involves integrating information over a window of time. For example, a window of roughly five seconds may be used and contain enough information to identify a seizure. Thus, for the analog implementations of these features, time constants for decaying integration may be chosen on the order of five seconds.

Emerging from each feature will be a voltage level $v_f(t)$ corresponding to the feature value at time t. This voltage may be prepared for Bayesian inference by being transformed to represent $P^*(E_f^v)(t)$ introduced in equation (2). During the pre-surgery study period, the function $p:v_f \rightarrow P^*(E_f^v)$ may be defined for each useful feature for each channel indicating how likely a seizure is, given the observed feature value $v_f(t)$. The function p may be hardcoded into a voltage-in, voltage-out lookup table (LUT) used to implement the analog voltage generation circuit 310. For instance, the analog voltage generation circuit 310 may have a low-power analog implementation. In some cases, only a small number of bins per feature may be created for high-accuracy detection, so a series of low-power level detectors can be substituted without loss of accuracy.

Once the voltages representing $P^*(E_f^v)(t)$ are obtained, they are fed into the bitstream generator 312 which may be implemented as a voltage-controlled tunable RNG that produces stochastic bitstreams with a time-varying probability equal to $P^*(E_f^v)(t)$. In some aspects, the bitstreams are fed asynchronously into the C-E(s) to perform naive Bayesian inference. The output of this network (e.g., output of the C-E circuit 314) will be a final stochastic bitstream representing the probability that the patient is currently in an ictal (seizure) state. Passing this bitstream through a passive low-pass filter (e.g., filter 316) converts the bitstream to a voltage level. A voltage level above a pre-determined threshold will represent a seizure state. After the threshold is applied, this Boolean signal may be fed into a treatment subsystem (e.g., signal generator 106) to stimulate the seizure network and stifle the seizure before it causes adverse symptoms.

The seizure detection system described herein may be implemented using intracranial EEG data or scalp EEG data. Scalp EEG signals contain more noise than intracranial EEG data, as the electric potentials are measured face interference from bone and skin. Therefore, a system that can reliably detect seizures with low power on scalp EEG data would be expected to perform equally well, if not better, on intracranial EEG data, albeit with some modifications to thresholds.

Figure 5:
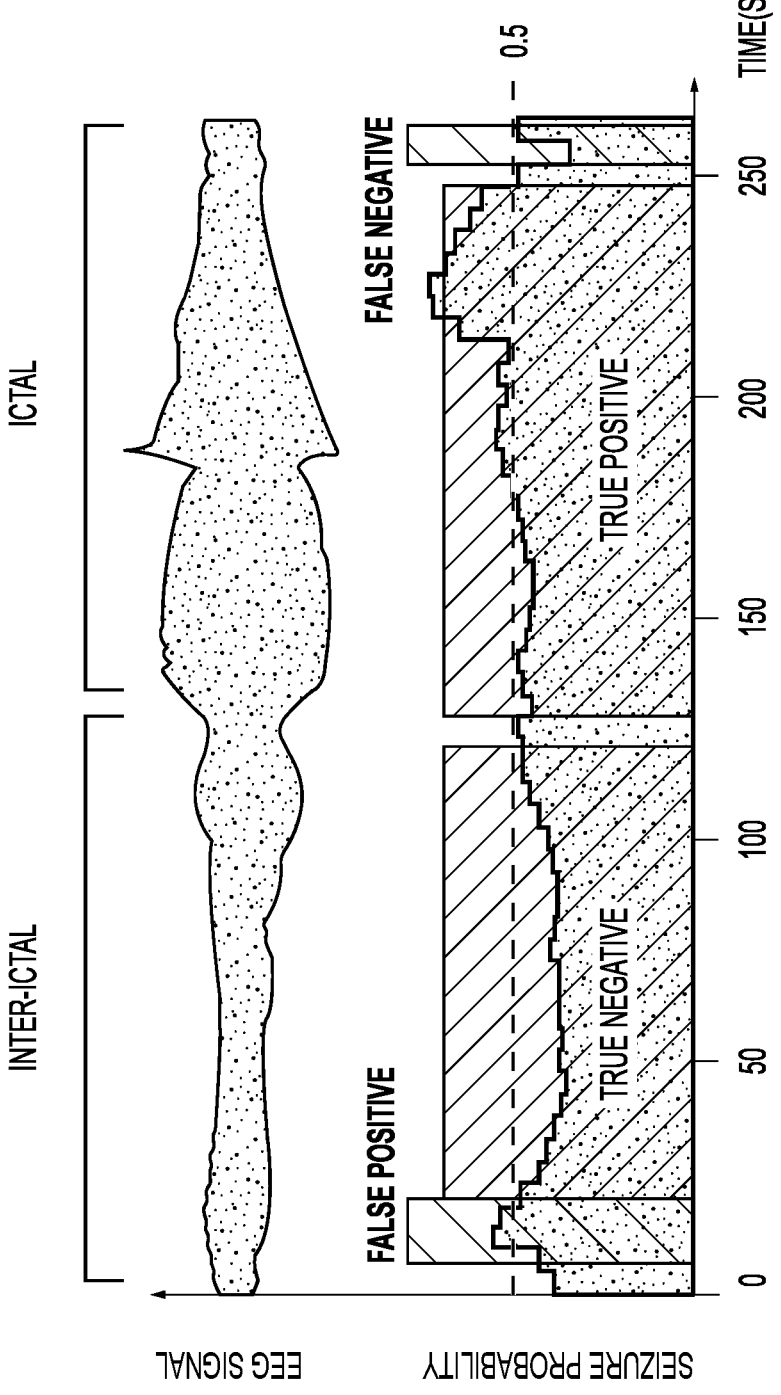
FIG. 5 illustrates techniques for seizure detection with discrete time windows, in accordance with certain aspects of the present inventive concept.

FIG. 5 illustrates techniques for seizure detection with discrete time windows, in accordance with certain aspects of the present inventive concept. For each 5-second window, the system identifies whether there is a seizure or not, which may be performed for both Ictal and Inter-Ictal states keeping false negatives and false positives to a minimum. Simulations of the seizure detection system may be performed in the digital domain. Each EEG signal may be processed using a bipolar Temporal Central Parasagittal (TCP) linked-ears reference montage so that each EEG recording contains 22 channels of EEG activity.

Each patient's seizure and non-seizure activity may be grouped into 5-second windows, as shown, and labeled as containing seizure or non-seizure data. For each patient, each feature may be evaluated on each channel for each 5-second window. In some aspects, the feature detection may not rely on Fourier or wavelet transforms to avoid incurring high computational costs associated with each transformation into the frequency/spectral domain.

The calculated features may be evaluated according to how well they could be used to detect seizures. For the model, a probability table corresponding to the probability distribution function for each feature-channel pair may be generated from the training set. This table gives the probability of observing a specific feature value in an ictal vs. inter-ictal state, or P(feature|ictal). A non-uniform binning algorithm may be used to provide a statistically useful amount of data in each bin and limit the overall number of bins.

FIG. 6 illustrates a windowed single feature performance of the seizure detection system, in accordance with certain aspects of the present inventive concept. The highest detection accuracies for each feature for each patient spanning 24 EEG channels are depicted, demonstrating that simple features can be used to obtain high detection accuracies for some patients. Naïve Bayesian inference may be computed directly from this probability distribution to classify each window in the testing set as showing either ictal or inter-ictal data. The J-statistic may be used to consolidate false negatives or false positives into a single metric on [−1,1] where a value of −1 implies no classifications were made correctly, and a value of 1 corresponds to perfect classification. Results for each patient are shown. For each feature, only the J-statistic for the channel with the highest performance is shown for brevity. High classification accuracies may be obtained for some feature-channel combinations for some patients indicating the ability for these features to be used to classify focal seizures.

Figure 7:
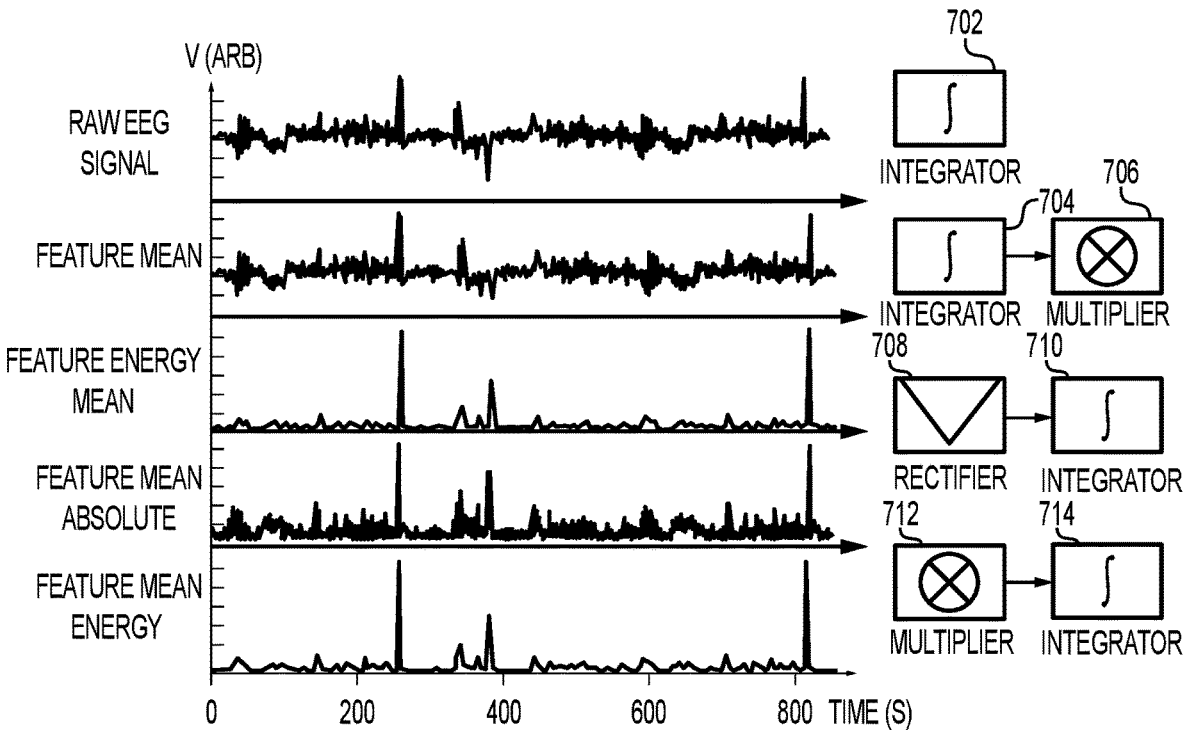
FIG. 7 illustrates analog features that may be used for seizure detection, in accordance with certain aspects of the present inventive concept.

FIG. 7 illustrates analog features that may be used for seizure detection, in accordance with certain aspects of the present inventive concept. A raw EEG signal along with extracted features is shown. As shown, the mean feature may be generated from the raw EEG signal using an integrator circuit 702. The energy mean feature may be generated from the raw EEG signal using an integrator circuit 704 followed by a multiplier circuit 706. The mean absolute feature may be generated from the raw EEG signal using a rectifier circuit 708 followed by an integrator circuit 710. The mean energy feature may be generated from the raw EEG signal using a multiplier 712 followed by an integrator circuit 714.

FIG. 8 illustrates an analog single feature performance of the seizure detection system, in accordance with certain aspects of the present inventive concept. For each feature, only the highest accuracy obtained among the 24 EEG channels is depicted. Patients 1543, 3401, 5625, and 7623 saw significant increases in accuracy when integrating information from multiple channels and features.

In some cases, simulations may be performed in the analog domain using Matlab's Simulink where EEG signals are not discretely sampled into 5-second windows, but rather, the various time constants of the feature circuits emulated a memory window of approximately 5-seconds. FIG. 7 depicts how a number of these features transform the input EEG signals. After circuit simulation, the feature values are binned and used to perform naive Bayesian inference.

FIG. 9 illustrates an analog multi-feature performance of the seizure detection system, in accordance with certain aspects of the present inventive concept. As shown, patients 1543, 3401, 5625, and 7623 experienced significant increases in accuracy when integrating information from multiple channels and features.

Classification based on a single (feature, channel) pair may be effective for patients with focal seizures, but may not be effective for patients whose seizures are distributed across the brain. Analog domain simulations may be extended to use multiple features across multiple channels simultaneously using naive Bayesian inference. All combinations of two features were evaluated to identify the highest performing pair. A genetic algorithm optimizer may be seeded with the highest performing two feature pair and used to find high-performing three and four feature combinations for a patient. The results of these optimizer simulations is shown in FIG. 9.

Figure 10:
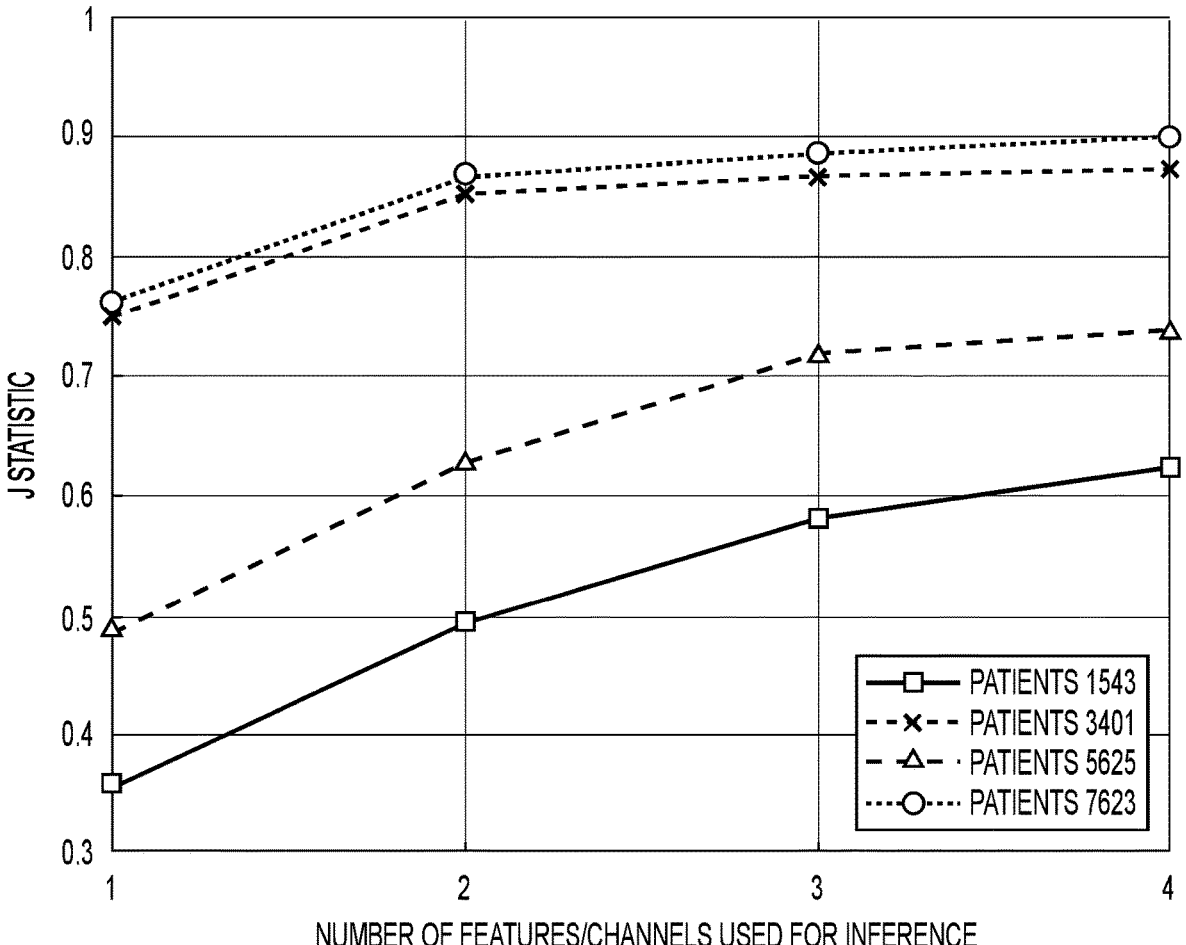
FIG. 10 illustrates J statistic versus the number of features for selected patients, in accordance with certain aspects of the present inventive concept.

FIG. 10 illustrates J statistic versus the number of features for selected patients, in accordance with certain aspects of the present inventive concept. The accuracies for the patients highlighted in FIGS. 8 and 9 are shown and are tracked according to how many features were used in each evaluation. Some patients saw up to a 30% increase in accuracy, and trends indicate that these accuracies will continue to increase with the further addition of features As described herein, a high percentage of patients experience an increase in seizure classification accuracy using two feature-channel pairs. Several patients continue to see an increase in accuracy through the case of four feature-channel pairs, some of which are highlighted in FIG. 8. Combinations of five or more (feature, channel) pairs may be used to increase these accuracies. For patients with seizure networks, multiple features and channels may be used to boost detection accuracy, decreasing false positives and the number of stimulations issued to the brain. Assuming a battery with 3.3 Wh capacity, the detection system is able to maintain high-accuracy detection using only pµW of power.

The first step of obtaining EEG signals is to detect brain activity through electrodes. After the electrodes detect the signals, a preliminary low-noise amplifier (e.g., amplification system 304) is used to amplify mV or µV signals to sub-volt levels for the cascading circuits to efficiently and accurately process the EEG signals. The consumption for the EEG signal amplification process may be less than 1 µA per channel. The EEG signals may have an upper bandwidth limit of 100 Hz. Sampling such EEG signals may not introduce notable extra energy with Nyquist sampling. The estimated power consumption for sensing and pre-amplification is therefore bound at 1.2 µW per (feature,channel). In some implementations, the seizure detection system may have a supply voltage of 1.2 V, a sampling frequency of 1000 Hz, average stimulation current of 1 mA, maximum stimulation current 12 mA, lead resistance of 1100 ohms, a stimulation pulse width of 160 µs, stimulation period of 5 ms, average stimulation duration 100 ms, maximum stimulation duration of 5000 ms, parasitic capacitance of 100 fF, load capacitance of 20 pF, and battery capacity of 3.3 Wh. In some cases, detection of mean feature may consume 1.995 µW, mean absolute feature may consume 3.539 µW, mean energy may consume 1.680 µW, and energy mean may consume 2.879 µW.

To convert the results from the feature extraction circuits to a voltage that modulates the switching probability of the RNGs, an analog-to-analog lookup table circuit is used such as the analog voltage generation circuit 310. The analog voltage generation circuit 310 may be implemented differently for each patient and for each feature. In some cases, a set of discrete level detectors may be used. A multilevel voltage reference circuit may be used to generate both the referencing and driving voltages, while a selector network may be used to map the input and output voltages arbitrarily. This circuit may consume 493.80 nW of power which scales linearly with the number of discrete input levels. In some cases, 40 discrete bins may be used to group feature and probability data. Using linear scaling then the power consumption may be 2.469 μW per (feature,channel).

As described, the bitstream generator may be implemented RNGs. RNGs may be used for the Bayesian inference circuit with C-Es. In some cases, stochastic p-bits may be used to implement the RNG. Stochastic p-bits may be used to generate true random numbers with low energy cost given the low energy barrier of the nanomagnets. A true random number generator (TRNG) may consume 20 fJ/bit. Assuming a 1000 Hz sample rate which may produce sufficiently long bitstreams for proper classification, power consumption per (feature, channel) pair for the TRNG can be estimated as:

$$P_{TRNG} = E_{bit} \cdot f_s = 20 \text{ pW}, \tag{3}$$

Where $P_{TRNG}$ is the power consumption for the TRNG block, $E_{bit}$ is the energy required to generate one bit of a random number, and $f_s$ is the sample rate. Compared to other analog blocks, the RNG consumes less power regardless of whether the RNGs are constructed by emerging technology devices or conventional CMOS circuits.

As described, the seizure detection system includes a multi-input C-element circuit as shown in FIG. 3. Each two-input C-Element consumes 20 fJ per bit operation. Since the power consumed by the C-element blocks is more than three orders of magnitude less than the major power consumption of the system, the power consumption of one n-input C-element for n channels can be estimated to be the same as n two-input for all channels, which can be normalized to one C-element per (feature, channel) pair. Therefore, the power consumed by each (feature, channel) pair of the C-Elements ($P_{C\text{-}Element}$) may be estimated as $$P_{C\text{-}Element} = 1000 \text{ Hz} \cdot 20 \text{ fj} = 20 \text{ pW}. \tag{4}$$

The typical responsive stimulation to seizures is a series of pulses with a frequency of 200 Hz, individual pulse-widths of 160 μs, 6 mA amplitude, and total active duration of 100 ms. For a 1200 ohm lead resistance, each stimulation activity consumes:

$$E_{stim,avg} = I_{stim}^2 \cdot R_{lead} \cdot T \cdot D = 138 \text{ μJ}, \tag{5}$$

where $E_{stim,avg}$ is the energy required to generate a series of pulses for one stimulation activity with average strength; $I_{stim}$ is the stimulating current amplitude; $R_{lead}$ is the lead resistance; T is the duration of one stimulation activity; and D=160 μs·200 Hz=3.2% is the duty cycle. When tuned for the patients who need more stimulations, with $I_{stim}$=12 mA, and a 200 μs pulse width, the energy consumption is:

$$E_{stim,high} = 691 \text{ μJ} \tag{6}$$

The total power consumption per (feature, channel) pair for the seizure detection system may be:

$$P_{total} = P_{sen} + P_{pre\text{-}amp} + P_{FE\text{-}avg} + P_{LUT} + P_{TRNG} +$$
$$P_{C\text{-}Element} = 6.189 \text{ μW} \tag{7}$$

Here, $P_{sen}$, $P_{pre\text{-}amp}$, $P_{FE\text{-}avg}$, $P_{LUT}$, $P_{TRNG}$, and $P_{C\text{-}Element}$ represent the power consumption on sensing, pre-amplification, (average) feature extraction, lookup table, true random number generator, and C-element blocks respectively. The detection system may use about 6.189 μW of power per (feature, channel) for detection. The detection accuracies continue to improve with an increasing number of (feature, channel) pairs. Assuming that an average of four (feature, channel) pairs are used per patient, the detection circuitry consumes roughly 25 μW. For stimulation, average seizure-activity patients may use 138 μJ per stimulation 570 times a day, giving a power consumption of 0.9 μW. Similarly, high seizure-activity patients may use 691 μJ per stimulation 1330 times a day giving a power consumption of 11 μW. Assuming a battery capacity of 3.3 Wh, the battery for low-activity patients may last over 14 years, and the battery for high activity patients may last over 10 years, both of which are significant improvements from conventional implementations. Implementing a low-power seizure detection engine that will simultaneously increase detection accuracies, decrease false positives and over-stimulation, and boost battery life by up to 50% compared with state-of-the-art responsive neurostimulation systems has been described. Each of these improvements will increase a patient's quality of life.

FIG. 11 is a flow diagram illustrating example operations 1100 to detect seizures, in accordance with certain aspects of the present inventive concept. The operations 1100 may be performed by, for example, a seizure processing system which may include the processing device 120.

The operations 1100 begin, at block 1102, with the seizure processing system obtaining (e.g., at seizure detection system 104), one or more electroencephalogram (EEG) signals. At block 1104, the seizure processing system detects (e.g., via feature detection circuit 308) a plurality of features associated with each of the one or more EEG signals.

At block 1106, the seizure processing system generates (e.g., via bitstream generator 312) a bitstream indicating a seizure probability associated with each feature of the plurality of features to yield a plurality of bitstreams indicating a plurality of seizure probabilities. In some aspects, the seizure processing system generates (e.g., via analog voltage generation circuit 310) an analog signal for each feature of the plurality of features. The bitstream may be generated based on the analog signal, and the analog signal includes a voltage corresponding to the seizure probability. For example, bitstream generator 312 may be implemented as a voltage-controlled tunable RNG, and the analog signal may be used to tune the RNG. A quantity of bits, in a specific time period, of the bitstream may have a specific logic state that indicates the seizure probability. A probability that each bit of the bitstream has a specific logic state may be equal to the seizure probability.

At block 1108, the seizure processing system generates (e.g., via feature evaluation circuitry 340) a seizure detection output based on the plurality of bitstreams indicating the plurality of seizure probabilities of the plurality of features. In some aspects, the seizure detection output may be generated via a Muller C-element circuit (e.g., C-E circuit 314) through stochastic computing. The seizure processing system may generate (e.g., via C-E circuit 314) a feature evaluation signal based on a comparison of the plurality of bitstreams. The seizure detection output is generated based on the feature evaluation signal. Generating the feature evaluation signal may involve (e.g., as described with respect to FIG. 2B) setting the feature evaluation signal to a specific logic state (e.g., logic high or logic low) when corresponding bits of the plurality of bitstreams have a same logic state, and setting the feature evaluation signal to a previous logic state when the corresponding bits of the plurality of bitstreams have different logic states. In some cases, the seizure processing system filters (e.g., via filter 316) the feature evaluation signal to yield a filtered feature evaluation signal, and the seizure detection output may be generated based on the filtered feature evaluation signal.

In some cases, the feature evaluation circuitry includes a set of PMOS transistors (e.g., PMOS transistors 202) coupled in series between a voltage rail and a common node, where a gate of each of the set of PMOS transistors are configured to receive a respective one of the plurality of bitstreams. The feature evaluation circuitry may also include a set of NMOS transistors (e.g., NMOS transistors 204) coupled in series between the common node and a reference potential node, wherein a gate of each of the set of NMOS transistors are configured to receive the respective one of the plurality of bitstreams. A latch (e.g., latch 206) comprising a pair of inverters may be coupled between the common node and an output of the feature evaluation circuitry.

The operations 1100 also include selecting, based on measurements associated with a patient, the plurality of features from candidate features. Before implanting the seizure detection system for the patient, the seizure detection system may be configured to use the plurality of features for seizure detection based on the selection.

In some cases, the seizure processing system performs measurements associated with the plurality of features. Detecting the plurality of features may include detecting whether each of the measurements meets a measurement threshold or is within a measurement range. The operations 1100 may also include selecting, based on measurements associated with a patient, the measurement threshold or the measurement range associated with each of the plurality of features. Before implanting the seizure detection system for the patient, the seizure detection system may be configured to use the measurement threshold or the measurement range for detecting each of the plurality of features based on the selection.

In some cases, the seizure processing system may also include a signal generator (e.g., signal generator 106) configured to generate an electrical stimulation signal in response to the seizure detection output and apply the electrical stimulation signal to a patient. In some cases, the seizure processing system also includes a wireless receiver (e.g., wireless receiver 112) coupled to the signal generator and configured to receive a wireless signal from a wireless transmitter (e.g., wireless transmitter 110). The signal generator may be further configured to tune the electrical stimulation signal based on the wireless signal.

These and various other arrangements will be described more fully herein. As will be appreciated by one of skill in the art upon reading the following disclosure, various aspects described herein can be a method, a computer system, or a computer program product. Accordingly, those aspects can take the form of an entirely hardware implementation, an entirely software implementation, or at least one implementation combining software and hardware aspects. Furthermore, such aspects can take the form of a computer program product stored by one or more computer-readable storage media (e.g., non-transitory computer-readable medium) having computer-readable program code, or instructions, included in or on the storage media. Any suitable computer-readable storage media can be utilized, including hard disks, CD-ROMs, optical storage devices, magnetic storage devices, and/or any combination thereof. In addition, various signals representing data or events as described herein can be transferred between a source and a destination in the form of electromagnetic waves traveling through signal-conducting media such as metal wires, optical fibers, and/or wireless transmission media (e.g., air and/or space).

Implementations of the present inventive concept include various steps, which are described in this specification. The steps may be performed by hardware components or may be embodied in machine-executable instructions, which may be used to cause a general-purpose or special-purpose processor programmed with the instructions to perform the steps.

Alternatively, the steps may be performed by a combination of hardware, software and/or firmware.

While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an implementation in the present inventive concept can be references to the same implementation or any implementation; and such references mean at least one of the implementations.

Reference to "one implementation" or "an implementation" means that a particular feature, structure, or characteristic described in connection with the implementation is included in at least one implementation of the disclosure. The appearances of the phrase "in one implementation" in various places in the specification are not necessarily all referring to the same implementation, nor are separate or alternative implementations mutually exclusive of other implementations. Moreover, various features are described which may be exhibited by some implementations and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various implementations given in this specification.

Without intent to limit the scope of the disclosure, examples of instruments, apparatus, methods and their related results according to the implementations of the present inventive concept are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

What is claimed is:

1. A method to detect seizures comprising:
  obtaining, at a seizure detection system, one or more electroencephalogram (EEG) signals;

detecting a plurality of features associated with each of the one or more EEG signals;

generating a bitstream indicating a seizure probability associated with each feature of the plurality of features to yield a plurality of bitstreams indicating a plurality of seizure probabilities; and generating, via feature evaluation circuitry, a seizure detection output based on the plurality of bitstreams indicating the plurality of seizure probabilities of the plurality of features, the feature evaluation circuitry including:

one or more p-channel metal-oxide semiconductor (PMOS) transistors coupled in series between a voltage rail and a common node, wherein a gate of the one or more PMOS transistors is configured to receive at least one of the plurality of bitstreams, one or more n-channel metal-oxide semiconductor (NMOS) transistors coupled in series between the common node and a reference potential node, wherein a gate of the one or more NMOS transistors is configured to receive the at least one of the plurality of bitstreams, and a latch comprising one or more inverters coupled between the common node and an output of the feature evaluation circuitry.

2. The method of claim 1, further comprising:

generating an analog signal for each feature of the plurality of features, wherein, the bitstream is generated based on the analog signal, and the analog signal includes a voltage corresponding to the seizure probability.

3. The method of claim 1, wherein a quantity of bits, in a specific time period, of the bitstream having a specific logic state indicates the seizure probability.

4. The method of claim 1, wherein a probability that each bit of the bitstream has a specific logic state is equal to the seizure probability.

5. The method of claim 1, wherein the seizure detection output is generated via a Muller C-element circuit through stochastic computing.

6. The method of claim 1, further comprising:

generating a feature evaluation signal based on a comparison of the plurality of bitstreams, wherein, the seizure detection output is generated based on the feature evaluation signal.

7. The method of claim 6, wherein the generating of the feature evaluation signal includes:

setting the feature evaluation signal to a specific logic state when corresponding bits of the plurality of bitstreams have a same logic state; and setting the feature evaluation signal to a previous logic state when the corresponding bits of the plurality of bitstreams having different logic states.

8. The method of claim 6, further comprising:

filtering the feature evaluation signal to yield a filtered feature evaluation signal, wherein, the seizure detection output is generated based on the filtered feature evaluation signal.

9. The method of claim 1, further comprising:

selecting, based on measurements associated with a patient, the plurality of features from candidate features; and before implanting the seizure detection system for the patient, configuring the seizure detection system to use the plurality of features for seizure detection based on the selection.

10. The method of claim 1, further comprising:

performing measurements associated with the plurality of features, wherein, detecting the plurality of features comprises detecting whether each of the measurements meets a measurement threshold or is within a measurement range.

11. The method of claim 10, further comprising:

selecting, based on measurements associated with a patient, the measurement threshold or the measurement range associated with each of the plurality of features; and before implanting the seizure detection system for the patient, configuring the seizure detection system to use the measurement threshold or the measurement range for detecting each of the plurality of features based on the selection.

12. An apparatus to detect seizures comprising:

a feature detection circuit configured to detect a plurality of features associated with one or more electroencephalogram (EEG) signals;

a bitstream generator configured to generate a bitstream indicating a seizure probability associated with each feature of the plurality of features to yield a plurality of bitstreams indicating a plurality of seizure probabilities; and feature evaluation circuitry configured to generate a seizure detection output based on the plurality of bitstreams indicating the plurality of seizure probabilities of the plurality of features, the feature evaluation circuitry including:

a set of p-channel metal-oxide semiconductor (PMOS) transistors coupled in series between a voltage rail and a common node, wherein a gate of each of the set of PMOS transistors are configured to receive a respective one of the plurality of bitstreams, a set of n-channel metal-oxide semiconductor (NMOS) transistors coupled in series between the common node and a reference potential node, wherein a gate of each of the set of NMOS transistors are configured to receive the respective one of the plurality of bitstreams, and a latch comprising a pair of inverters coupled between the common node and an output of the feature evaluation circuitry.

13. The apparatus of claim 12, further comprising:

an analog voltage generation circuit configured to generate an analog signal for each feature of the plurality of features, wherein, the bitstream is generated based on the analog signal, and the analog signal includes a voltage corresponding to the seizure probability.

14. The apparatus of claim 13, wherein, the bitstream generator is configured to receive the analog signal and generate the bitstream based on the analog signal, a quantity of bits, in a specific time period, of the bitstream having a specific logic state indicates the seizure probability.

15. The apparatus of claim 12, wherein, the feature evaluation circuitry comprises a Muller c-element circuit configured to generate a feature evaluation signal, and the seizure detection output is generated based on the feature evaluation signal.

16. The apparatus of claim 12, wherein, the feature evaluation circuitry is configured to generate a feature evaluation signal based on a comparison of the plurality of bitstreams, and the seizure detection output is generated based on the feature evaluation signal.

17. The apparatus of claim 16, wherein the feature evaluation circuitry is configured to generate the feature evaluation signal by:

setting the feature evaluation signal to a specific logic state when corresponding bits of the plurality of bitstreams have a same logic state; and setting the feature evaluation signal to a previous logic state when the corresponding bits of the plurality of bitstreams having different logic states.

18. The apparatus of claim 16, wherein, the feature evaluation circuitry includes a low-pass filter configured to filter the feature evaluation signal and yield a filtered feature evaluation signal, and the seizure detection output is generated based on the filtered feature evaluation signal.

19. The apparatus of claim 12, wherein, the feature detection circuit is configured to perform measurements associated with each of the plurality of features, and to detect the plurality of features, the feature detection circuit is configured to detect whether each of the measurements meets a measurement threshold or is within a measurement range.

20. The apparatus of claim 12, further comprising:

a signal generator configured to:

generate an electrical stimulation signal in response to the seizure detection output; and apply the electrical stimulation signal to a patient.

21. The apparatus of claim 20, further comprising:

a wireless receiver coupled to the signal generator and configured to receive a wireless signal from a wireless transmitter, wherein, the signal generator is configured to tune the electrical stimulation signal based on the wireless signal.

22. A seizure detection system comprising:

one or more electrodes configured to generate one or more electroencephalogram (EEG) signals;

an amplification circuit configured to amplify the one or more EEG signals to yield one or more amplified EEG signals;

a feature detection circuit configured to detect a plurality of features associated with each of the one or more amplified EEG signals;

a bitstream generator configured to generate a bitstream indicating a seizure probability associated with each feature of the plurality of features to yield a plurality of bitstreams indicating a plurality of seizure probabilities; and feature evaluation circuitry configured to generate a seizure detection output based on the plurality of bitstreams indicating the plurality of seizure probabilities of the plurality of features, the feature evaluation circuitry including:

one or more p-channel metal-oxide semiconductor (PMOS) transistors coupled in series between a voltage rail and a common node, wherein a gate of the one or more PMOS transistors is configured to receive at least one of the plurality of bitstreams, one or more n-channel metal-oxide semiconductor (NMOS) transistors coupled in series between the common node and a reference potential node, wherein a gate of the one or more NMOS transistors is configured to receive the at least one of the plurality of bitstreams, and a latch comprising one or more inverters coupled between the common node and an output of the feature evaluation circuitry.

\* \* \* \* \*